US012797513B2

(12) United States Patent
Morlok et al.

(10) Patent No.: US 12,797,513 B2
(45) Date of Patent: Nov. 17, 2026

(54) PROCESSING ARRANGEMENT

(71) Applicant: H & B Electronic Gmbh & Co. KG, Deckenpfronn (DE)

(72) Inventors: Tobias Morlok, Mötzingen (DE); Jan Bayerbach, Calw (DE); Jochen Heimsch, Fellbach (DE); Nico Remy, Tübingen (DE)

(73) Assignee: H & B ELECTRONIC GMBH & CO. KG, Deckenpfronn (DE)

( * ) Notice: Subject to any disclaimer, the term of this patent is extended or adjusted under 35 U.S.C. 154(b) by 659 days.

(21) Appl. No.: 18/226,599

(22) Filed: Jul. 26, 2023

(65) Prior Publication Data

US 2024/0058506 A1 Feb. 22, 2024

(30) Foreign Application Priority Data

Aug. 19, 2022 (DE) ......................... 102022121044.8

(51) Int. Cl.
*A61L 27/36* (2006.01)

(52) U.S. Cl.
CPC ....... *A61L 27/3691* (2013.01); *A61L 27/3608* (2013.01); *A61L 27/3612* (2013.01)

(58) Field of Classification Search
CPC ............. A61L 27/3691; A61L 27/3608; A61L 27/3612
See application file for complete search history.

(56) References Cited

U.S. PATENT DOCUMENTS

| | | | | |
|---|---|---|---|---|
| 7,771,716 | B2 * | 8/2010 | Hedrick | A61L 27/54 606/1 |
| 9,463,203 | B2 * | 10/2016 | Hedrick | A61L 27/3852 |
| 9,504,716 | B2 * | 11/2016 | Hedrick | A61P 19/04 |
| 10,172,594 | B2 * | 1/2019 | Videbaek | B01L 3/523 |
| 10,772,997 | B2 * | 9/2020 | Shippert | A61M 1/892 |
| 10,927,347 | B2 * | 2/2021 | Pilkington | A61M 1/892 |
| 2002/0161449 | A1 * | 10/2002 | Muschler | A61L 27/365 623/23.51 |
| 2005/0025755 | A1 * | 2/2005 | Hedrick | A61L 27/3834 435/366 |
| 2005/0048033 | A1 * | 3/2005 | Fraser | A61L 27/3834 424/93.7 |

(Continued)

FOREIGN PATENT DOCUMENTS

| | | |
|---|---|---|
| JP | 2006-230686 A | 9/2006 |
| WO | WO 2020/227196 A1 | 11/2020 |

*Primary Examiner* — Guy K Townsend

(74) *Attorney, Agent, or Firm* — Birch, Stewart, Kolasch & Birch, LLP

(57) ABSTRACT

A processing arrangement for tissue material removed from a patient and to be applied after processing, such as in particular an autologous cartilage or bone tissue, includes a collection container which has a collection receptacle for receiving the tissue material removed from a tissue removal device, a processing container which has a mixing receptacle for receiving the tissue material and a liquid to pasty medium, and a processing device for mixing of the tissue material and the medium. A connection device is provided, on which a first fastener for attaching the collection container and second fastener for attaching the processing container and one passage opening, which can be positioned between the collection receptacle and the mixing receptacle, are provided.

23 Claims, 7 Drawing Sheets

(56) References Cited

U.S. PATENT DOCUMENTS

Figure 1:
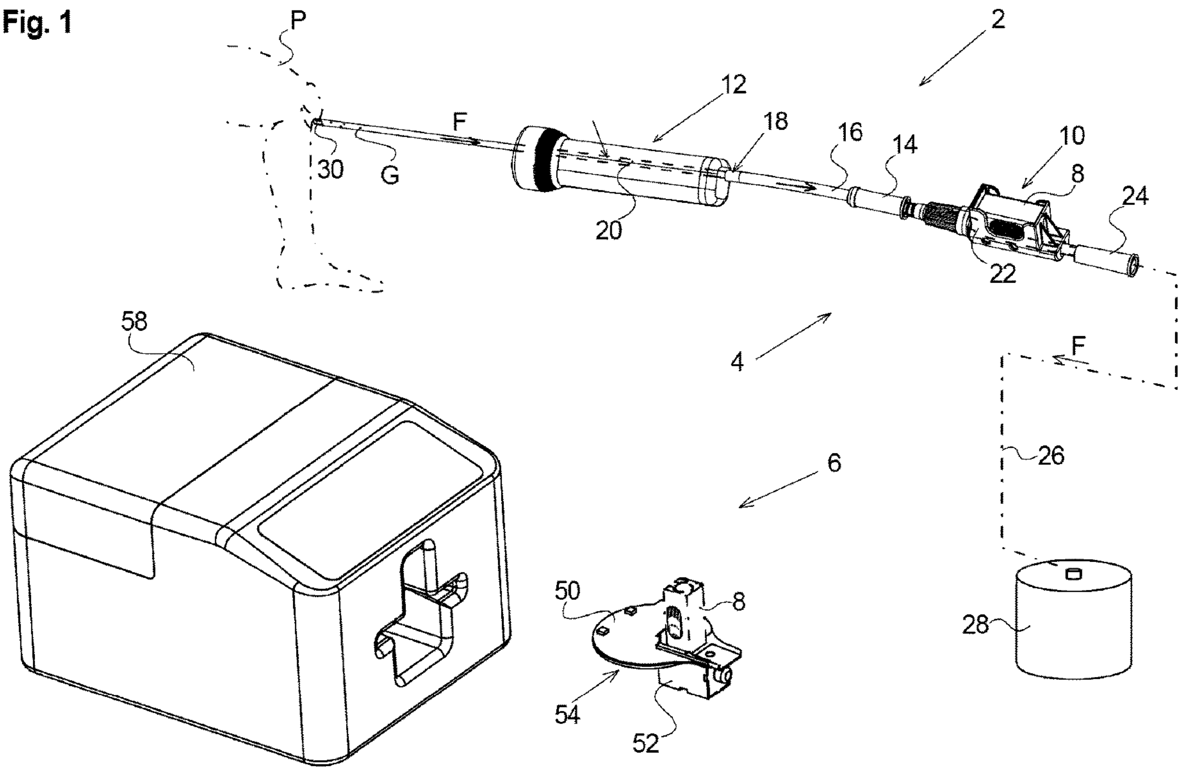

| | | | | |
|---|---|---|---|---|
| 2005/0048035 | A1* | 3/2005 | Fraser | A61L 27/56<br>435/368 |
| 2005/0048036 | A1* | 3/2005 | Hedrick | A61K 35/28<br>424/93.7 |
| 2005/0048644 | A1* | 3/2005 | Hedrick | A61L 27/54<br>435/366 |
| 2005/0095228 | A1* | 5/2005 | Fraser | A61P 9/10<br>424/93.7 |
| 2006/0083720 | A1* | 4/2006 | Fraser | A61K 35/28<br>435/366 |
| 2010/0285521 | A1* | 11/2010 | Vossman | C12M 45/02<br>435/308.1 |
| 2012/0323325 | A1* | 12/2012 | Fulton | A61L 27/60<br>623/15.12 |
| 2016/0159884 | A1* | 6/2016 | Schendel | A61K 35/35<br>514/8.4 |
| 2016/0325018 | A1* | 11/2016 | Assell | A61B 17/8805 |
| 2016/0333305 | A1* | 11/2016 | Pilkington | C12M 45/02 |
| 2017/0258849 | A1* | 9/2017 | Bare | B01L 3/50825 |
| 2018/0057787 | A1* | 3/2018 | Friedman | B01F 27/84 |
| 2019/0262050 | A1* | 8/2019 | Assell | A61J 1/1475 |
| 2020/0061258 | A1* | 2/2020 | Khalaj | A61M 1/88 |
| 2024/0058506 | A1* | 2/2024 | Morlok | A61B 17/32002 |

* cited by examiner

PROCESSING ARRANGEMENT

The invention relates to a processing arrangement for tissue material removed from a patient and to be reapplied after processing, such as in particular an autologous cartilage tissue of a joint or bone material, according to the preamble of claim 1 and a collection-processing system with such a processing arrangement. The processing arrangement has a collection container with a collection receptacle for receiving tissue material that has been removed by means of a tissue removal device or a shaver. In addition, the processing arrangement has a processing container that forms a mixed receptacle that serves to receive the tissue material together with a liquid to pasty medium that is formed, for example, by a hydrogel or contains an autologous conditioned plasma or blood serum. Furthermore, the processing arrangement has a processing device which is used for mixing or for suspending the tissue material in the medium in order to produce a pasty application mass.

Under the designation AutoCart™ a system is known which is used to obtain autologous tissue material, to produce a blood serum, to produce a pasty mass from the tissue material and the blood serum and to apply the pasty mass. In this case, the tissue material removed and comminuted by a tissue removal device is separated from a fluid flow into a collection container, from which it is then removed in order to place it in a syringe. This syringe is connected to a second syringe containing the blood serum via an adapter. By repeatedly pushing the syringe plungers back and forth on both sides, both syringe contents are mixed to form the pasty application mass.

A disadvantage of the known system is that contamination or germ contamination can occur when transferring the tissue material from the collection container into the syringe. This risk of contamination is even greater if, depending on the application, additional comminution of the particles of the tissue material should be necessary. In addition, the known procedure for mixing the tissue material with the blood serum is relatively time-consuming and often leads to insufficient homogeneity of the application mass.

The object of the invention is to avoid the disadvantages mentioned in a generic processing arrangement and to enable sterile processing of the tissue material and high homogeneity of the application mass produced.

This object is achieved by a processing arrangement having the features of claim 1. A connection device is provided, on which first fastening means for attaching the collection container and second fastening means for attaching the processing container and a passage opening positioned in a fastening position between the collection receptacle and the mixing receptacle are provided. In this way, the collection container can be connected to the processing container via the connection device in order to enable the tissue material to be discharged directly from the collection container into the processing container. In this way, a free removal of the tissue material from the collection container, which could lead to contamination, is avoided. Rather, the collection container and the processing container can be attached to the connection device by means of the fastening means in a sealed manner to the outside in order to enable a germ-free transfer of the tissue material.

In a particularly advantageous embodiment, a crushing tool is provided at the passage opening. As a result, the tissue material can additionally be comminuted to a desired particle size during the outwardly shielded transfer of the tissue material from the collection container to the receiving container. Thus, the tissue material does not have to be freely removed from the collection container for the purpose of additional comminution.

Preferably, the comminution tool is formed by a disk that is rotatably mounted on the connection device and has at least one cutting element. A maximum particle size for the entire transferred tissue material can be adjusted by the disk-shaped comminution tool. In addition, the disc-shaped comminution tool can be integrated particularly easily into the connection device, wherein it closes the through-opening in the non-driven state and transfers the tissue material to the processing container in connection with the comminution when activated. The disk-shaped comminution tool can advantageously be shifted into a specific rotational position in which the through-opening is essentially completely sealed. In this way it can be avoided that the tissue material escapes prematurely and uncomminuted from the collection container into the processing container and/or that the tissue material, the medium or the mixture produced from it gets from the processing container into the collection container during the mixing process.

In addition, it is advantageous if a mixing tool that can be driven from the outside protrudes into the mixing receptacle on the processing container. In this way, a mixing tool can be integrated into the processing container, which is adapted to the shape and size of the processing container and to the amount of tissue material to be processed and the medium to be mixed with it. In this way, an optimized impingement and mixing of the content received in the processing container can be guaranteed.

The mixing tool is advantageously formed by an agitator which is rotatably mounted on the processing container and can be driven by the processing device, as a result of which a particularly homogeneous mixing of the tissue material with the respective medium can be ensured.

In addition, the collection container preferably has a closing element which can be adjusted between a closed position, in which it closes the collection receptacle, and an open position, in which the collection receptacle is at least partially open. In this way, the collection container can be securely closed when it is separated from both the collection arrangement and the processing arrangement, in order to avoid contamination of the tissue material taken up, for example when transferring from the collecting arrangement to the processing arrangement.

It is advantageous if the closing element can be brought automatically into a second open position when connecting the first fastening means of the connection device to the first counter-fastening means of the collection container, in which a container opening of the collection container 8 is released. In this way, it is ensured that the collection receptacle is ready for delivery of the tissue material to the processing container when the collection container is in the connected state with the connection device.

The first fastening means and the first counter-fastening means advantageously form a first slide-in connection, wherein the closing element is formed by a sliding element which can be brought from the closed position into the second open position by an insertion movement of the first fastening means relative to the first counter-fastening means. In this way, the collection receptacle can also be permanently shielded from the outside during the production of the first push-in connection of the collection container with the connection device, in order to avoid contamination.

The processing container preferably has a closing element which can be adjusted between a closing position in which it closes the mixing receptacle and a receiving position in which the mixing receptacle is open. As a result, the processing container can also be securely closed when it is separated from the connection device or from the collection container, in order to prevent contamination of the medium accommodated therein prior to a processing process and/or contamination of the application mass then taken up after a processing process. In addition, the closing element of the collection container that can be brought into the second open position and the closing element of the processing container that can be moved into the receiving position allow the tissue that has been received or the application mass produced from it to be removed as required in any process step. In this way, the collected tissue material is available in whole or in part at any time for other processing or use, either in unprocessed form, in comminuted form or in a form that has already been mixed with the medium.

It is advantageous if the closing element can be brought into the receiving position automatically when the second fastening means of the connection device are connected to the second counter-fastening means of the processing container. In this way, it is ensured that the collection receptacle is ready for delivery of the tissue material to the processing container when the collection container is in the connected state with the connection device.

Advantageously, the second fastening means and the second counter-fastening means form a second push-in connection, the closing element being formed by a closure slide which can be brought from the closed position into the receiving position by an insertion movement of the second fastening means relative to the second counter-fastening means through contact with the connection device. In this way, the collection receptacle can also be permanently shielded from the outside during the production of the first push-in connection of the collection container with the connection device, in order to avoid contamination.

In a particularly preferred embodiment, the processing device has at least one drive and a processing receptacle for the connection device with a collection container and processing container attached thereto, the drive forming a first drive connection with the mixing tool in a receiving position. Due to the fact that the collection container and the processing container are accommodated together in the connected state within the processing device, permanent shielding of the container contents and the application mass produced therefrom can also be ensured during the processing. The drive of the processing device enables a mechanical mixing process.

In the receiving position, the at least one drive advantageously also has a second drive connection with the comminution tool. In this way, the tissue material can also be comminuted mechanically when it is released from the collection container by means of the processing device.

In addition, it is advantageous if the collection container has a piston for emptying the collection receptacle in the direction of the passage opening, in order to enable the tissue material that has been received to be completely ejected.

The processing container preferably has at least one closable input/output connection. The application mass can be received in a syringe-like applicator via the input/removal connection, for example, in order to be able to be subsequently applied from this into a lesion to be treated. Furthermore, if required, additional medium can be fed into the mixing receptacle via the at least one input/removal connection during a preparation process. In this case, for example, a first input/removal connection is provided, the shape, size and position of which is tailored to a specific applicator, and a second input/removal connection is provided, which is designed in its shape, size and position for the purpose of convenient input of the medium.

Advantageously, a slide for emptying the mixed receptacle is provided on the processing container, on which the at least one input/output connection is held in order to empty the mixed receptacle through it. As a result, the slide allows the pasty application mass produced to be removed essentially completely and the relevant applicator to be filled more easily and more evenly.

Advantageously, the processing device additionally has at least one actuator for actuating the piston and/or the slide in order to enable automatic or mechanical delivery of the tissue material from the collection container and/or delivery of the processed application material from the processing container. As a result, after the collection and processing containers connected to one another have been accommodated on the processing device, the entire processing process can be carried out largely automatically. The individual processing steps consisting of dispensing the tissue material, crushing the tissue material, mixing the tissue material with the medium and dispensing the application mass produced can be carried out at least partially automatically by the processing device. In addition or as an alternative, the slide can also be actuated manually, for example by means of an applicator to be filled. In this way, the mixing receptacle can also be completely emptied independently of the processing device, in particular in order to be able to dispense the application mass produced from the processing container as evenly and completely as possible to the applicator.

In this case, the processing device preferably has an electronic device for the at least partially automated activation of the at least one drive and/or the at least one actuator. As a result, all or some of the processing steps can be carried out partially or fully automatically and coordinated with one another in terms of time.

In a particularly preferred embodiment, a camera is also provided on the processing device, which is used for capturing images of the mixing receptacle. This enables permanent optical monitoring of the preparation process and the application mass produced in the process, for example on a screen connected to the camera. The screen can be formed, for example, by a touchscreen of the processing device, which is also used to enter control instructions. As an alternative or in addition to this, an automated evaluation of the recorded image information can also be provided in order to control or regulate the processing device during a processing process, for example.

Furthermore, the above-mentioned object is achieved by a collection/processing system with a processing arrangement in one of the above-mentioned embodiments, wherein the collection container can also be detachably fixed to a connection housing of a collection device that is arranged to separate and collect tissue from a fluid flow between a tissue removal device and a vacuum device. In this way, the tissue material in question can be collected in the collection container after removal via the tissue removal device, released into the collection container after the collection container has been removed from the rest of the collection device and connected to the processing container, processed in the processing device and then delivered to the applicator without that it must be freely removed from one of the containers. Rather, the tissue material or the application mass produced from it is continuously shielded from the outside and protected against contamination from the time it is collected until it is received in the applicator. In this way, the greatest possible sterility of the application mass can be guaranteed.

Advantageously, the collection container forms a flow portion of a connection path that can be produced in a collection position between a shaver-side flow connection that can be fluidly connected to the tissue removal device and a vacuum-side flow connection that can be fluidly connected to the vacuum device. As a result, the tissue material separated by the collection device from a fluid flow between the tissue removal device and the vacuum device can be received directly in the removable collection container during separation. In this way, the tissue material is immediately available for further processing after the collection container has been removed.

When the collection container is removed from the connection housing, the closing element of the collection container can preferably be moved automatically from a first open position, in which the inlet opening is released, into the closed position in order to be able to ensure that the received tissue material is received in a continuously protected manner. For this purpose, the closing element can be biased into the closed position, for example by a spring device.

It should be noted that all features of the subject matter according to the invention described above can be swapped or combined with one another, provided that a swap or a combination thereof is not ruled out for technical reasons.

Figure 2:
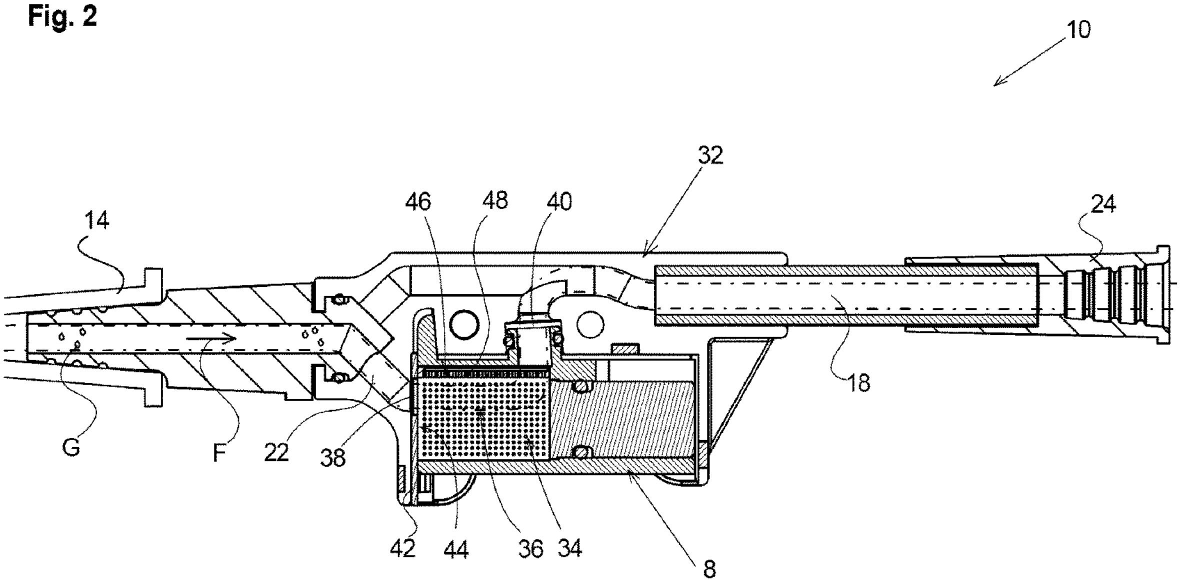
Figure 3:
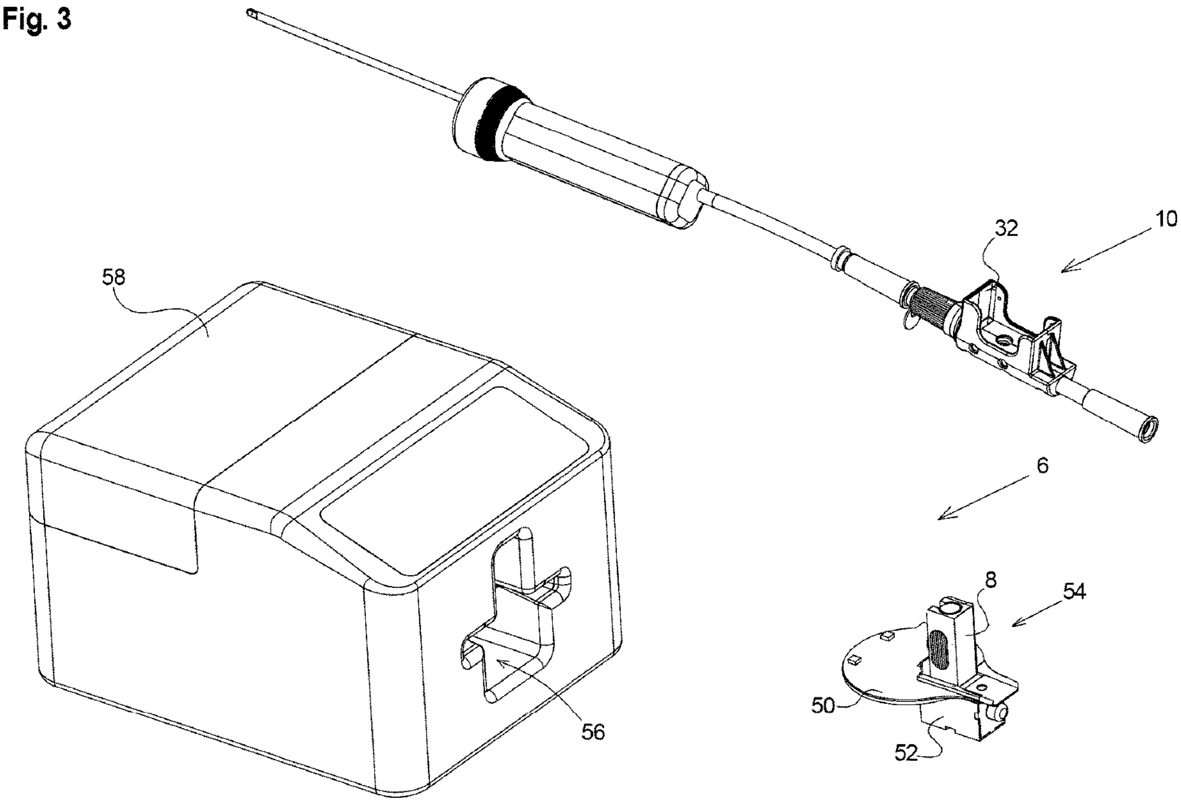
Figure 4:
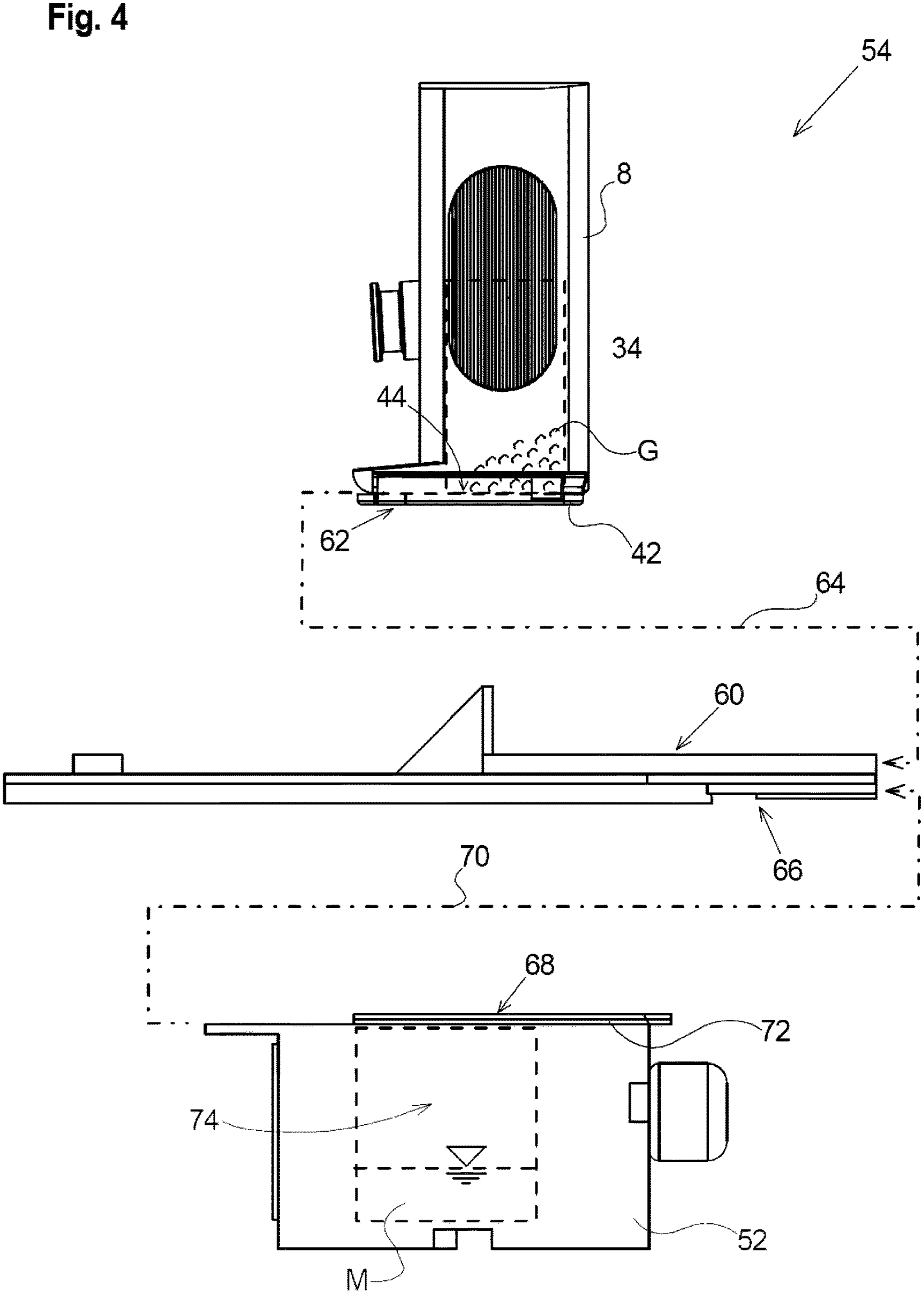
Figure 5:
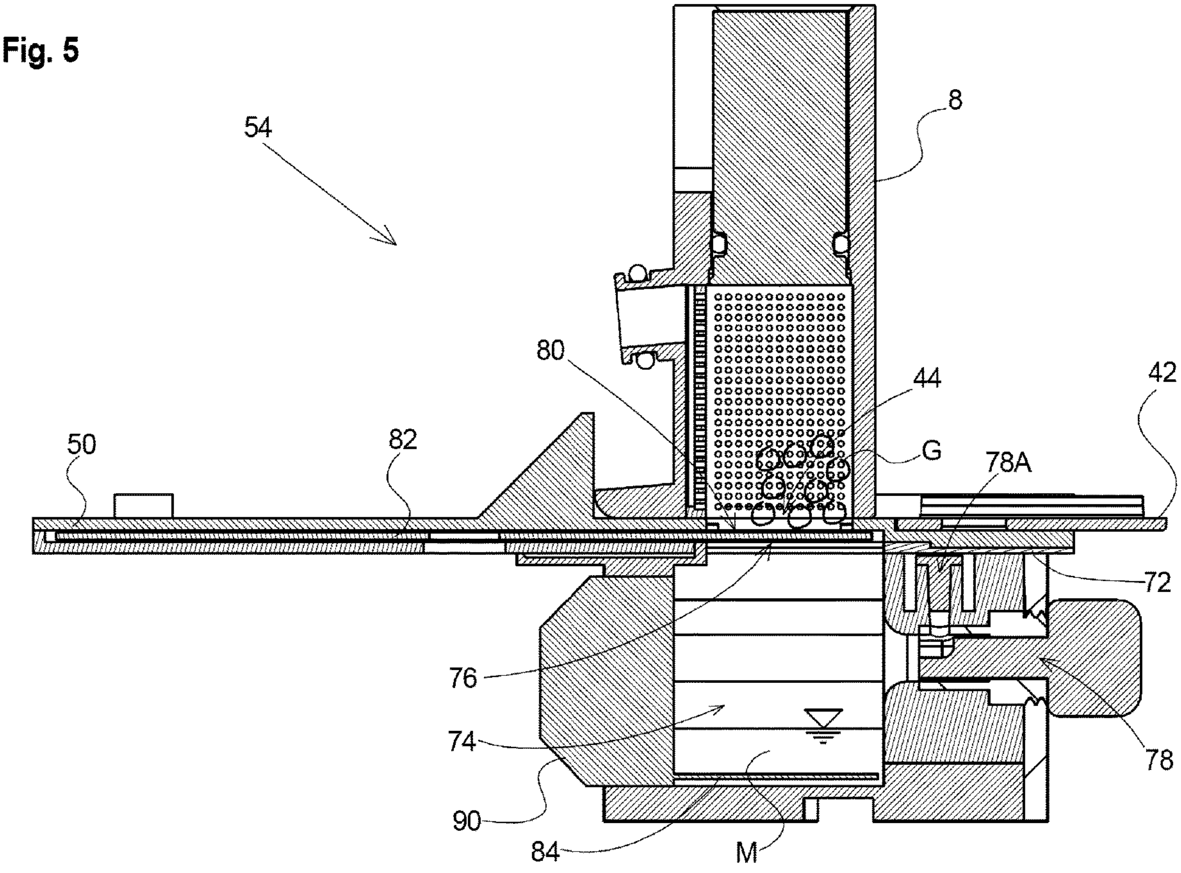
Figure 6:
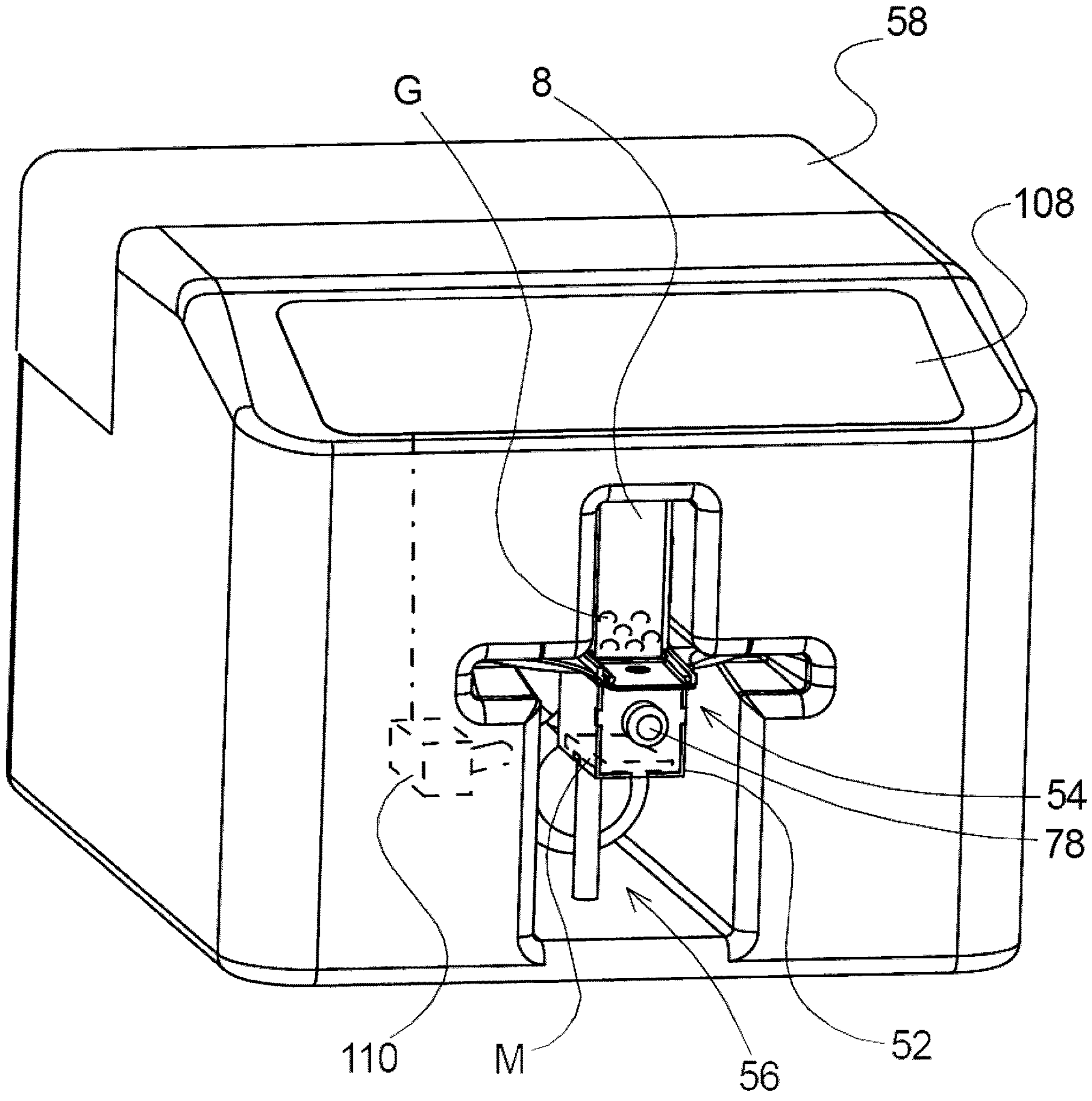
Figure 7:
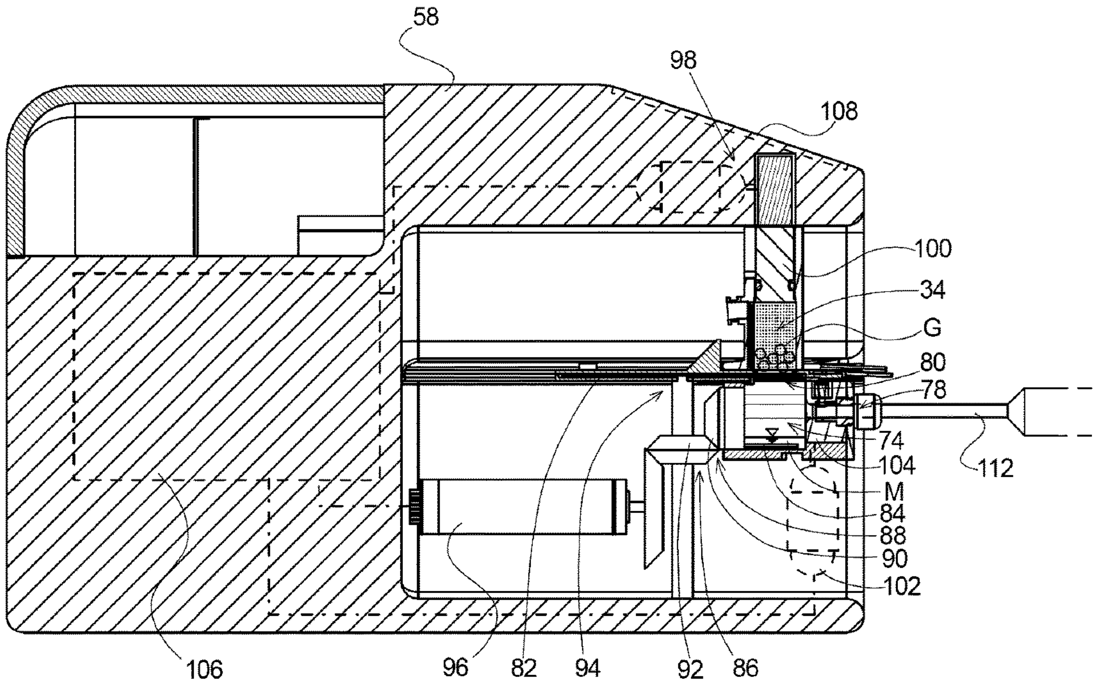

An exemplary embodiment of the invention is shown in the figures. In the figures:

FIG. 1 shows a perspective view of a collection/processing system with a processing arrangement according to the invention, FIG. 2 shows a longitudinal section through a collection device of the collection arrangement according to FIG. 1, FIG. 3 shows the collection/processing system according to FIG. 1 with a slide-in unit prepared for a processing process, FIG. 4 shows a view of the slide-in unit according to FIG. 3 in a separated state FIG. 5 shows a section through the slide-in unit according to FIG. 3 in the ready-to-use state, FIG. 6 shows a perspective view of a processing device of the processing arrangement with received slide-in unit and FIG. 7 shows a section through the processing device according to FIG. 6.

FIG. 1 shows a collection/processing system 2 for tissue material G to be removed from a patient P and to be applied after processing, such as in particular autologous cartilage tissue of a joint or bone material. The collection/processing system forms a collection arrangement 4 for collecting the tissue material G and a separate processing arrangement 6 for processing the collected tissue material G. The collection arrangement 4 and the processing arrangement 6 are used in connection with a common collection container 8.

The collection arrangement 4 has a collection device 10 for a tissue removal device 12 formed by a shaver, by means of which the tissue material G, such as in particular cartilage or bone tissue, can be removed from the patient P. The tissue material G is removed, for example, from a knee or shoulder joint or from a bone. The tissue material G obtained in this way is used later in the construction of tissue or bone in a defect in patient P.

To collect the tissue material G in the collection container 8, the collection device 10 has a flow connection 14 on the shaver side, which is connected fluidically via a connecting line 16 to a delivery connection 18 of a tissue outlet 20 of the tissue removal device 12. In addition, the collection device 10 has a vacuum-side flow connection 24 that can be connected to the shaver-side flow connection 14 via a connection path 22 and that is connected fluidically to a vacuum device 28 via a connecting line 26.

As soon as a vacuum is applied to the connection line 26 by means of the vacuum device 28, a fluid flow F is thereby generated from the tissue removal device 12 via the collection device 10 to the vacuum device 28. The tissue material G removed by a tool 30 can be transported to the discharge connection 18 by means of the tissue discharge 20 in order to feed it to the collection container 8 of the collection device 10.

As can be seen in particular from FIG. 2, the collection container 8 is fixed to a connection housing 32 in such a way that it forms a flow portion 36 between an inlet opening 38 and an outlet opening 40 with a collection receptacle 34. The inlet opening 38 is integrated into a closing element 42 which, in a first open position shown, only releases the inlet opening 38 and otherwise closes a container opening 44 of the collection container 8. The collection receptacle 34 is here partially delimited by a sieve device 46 which has at least one planar sieve surface 48 in front of the outlet opening 40 in the direction of flow of the fluid flow F.

As can also be seen from FIG. 2, the connection path 18 runs from the flow connection 14 on the shaver side via the flow portion 36 to the flow connection 24 on the vacuum side. in this way the tissue material G entrained in the fluid flow F can be separated by the sieve device 46 and collected in the collection receptacle 34.

As soon as a sufficient quantity of the tissue material G has been collected, the collection container 8 can be separated from the connection housing 32 of the collection device 10 in order to be attached to a connection device 50 of the separate processing arrangement 6 according to FIG. 3. The connection device 50 is used for jointly accommodating the collection container 8 and a processing container 52 in order to form a cassette-like slide-in unit 54. This can be inserted into a processing receptacle 56 of a processing device 58 in order to carry out a processing process.

In order to ensure that the collected tissue material G is protected and shielded from the outside when the collection container 8 is moved from the collection arrangement 4 to the processing arrangement 6, the closing element 42 automatically moves from the first open position according to FIG. 2 into a closed position when the collection container 8 is removed from the connection housing 32 in which both the container opening 44 and the inlet opening 38 are closed, as shown in FIG. 4. For this purpose, the closing element 42 can be biased in the direction of the closed position, for example, or entrainment means are provided which move the closing element 42 into the closed position by the relative movement with respect to the connection housing 32 (not shown). In any case, the tissue material G received in the collection receptacle 34 can no longer escape via the container opening 44 or the inlet opening 38 and is protected against contamination from the outside as soon as the closing element 42 is arranged in the closed position.

In order to fasten the collection container 8 to the connection device 50, this has first fastening means 60 which interact with first counter-fastening means 62 of the collection container 8. The first fastening means 60 and counter-fastening means 62 have, for example, interlocking rail elements that enable a first slide-in connection 64, during the production of which the slide-like closing element 42 of the collection container 8 can be automatically displaced into a second open position according to FIG. 5. In this second open position, the closing element 42 releases the container opening 44 at least as far as possible.

As also shown in FIG. 4, the processing container 52 can also be attached to a side of the connection device 50 facing away from the collection container 8 in order to form the slide-in unit 54.

In order to fasten the processing container 52, the connection device 50 has second fastening means 66 which interact with second counter-fastening means 68 of the processing container 52. The second fastening means 66 and counter-fastening means 68 also have interlocking rail elements, for example, which enable a second slide-in connection 70, during the production of which a closing element 72 of the processing container 52 is automatically displaceable from a closing position according to FIG. 4, in which a mixing receptacle 74 is closed, into a receiving position according to FIG. 5, in which a receiving opening 76 of the mixing receptacle 74 is released. For this purpose, the closing element 72 is designed in the form of a slide, for example, and can be displaced via a contact on the connection device 50 as a result of the insertion movement.

The mixing receptacle 74 of the processing container 52 serves to receive and process the tissue material G together with a liquid to pasty medium M, which is formed, for example, by a hydrogel or a blood serum. For this purpose, as shown in FIG. 5, the medium M can already be preportioned in the mixing receptacle 74 and/or can be introduced into the mixing receptacle 74 during a preparation process via at least one closable input/extraction connection 78 or 78A of the preparation container 52. In this case, for example, a first input/removal connection 78 is provided, the shape, size and position of which is tailored to a specific applicator 112 (see FIG. 7), and a second input/removal connection 78A is provided, which is designed in its shape, size and position for the purpose of convenient input of the medium.

As can also be seen from FIG. 5, the connection device 50 has a passage opening 80 which is arranged between the container opening 44 and the receiving opening 76 in the illustrated fastening position of the slide-in unit 54 with the collection container 8 and processing container 52 attached. In addition, the connection device 50 has a comminution tool 82 which extends over the through opening 80. The comminution tool 82 is designed, for example, in the shape of a disk and is held in the connection device 50 such that it can be rotated. The comminution tool 82 has at least one cutting element, preferably a large number of cutting elements. The disk-shaped comminution tool 82 can advantageously be shifted into a specific rotational position in which the through-opening 80 is essentially completely sealed. In this way it can be avoided that the tissue material G escapes prematurely and uncomminuted from the collection container 8 into the processing container 52 and/or that the tissue material G, the medium M or the mixture produced from it gets from the processing container 52 into the collection container 8 during the mixing process.

In addition, a mixing tool 84 is provided on the processing container 52, which is formed, for example, by a rotatably mounted whisk which protrudes into the mixing receptacle 74.

As can be seen from FIG. 6, the slide-in unit 54 can be pushed into the processing receptacle 56 of the processing device 58 in the manner of a cassette. In this receiving position, the tissue material G received in the collection container 8 and the medium M received in the processing container 52 can be processed into the desired application mass by being acted upon by the processing device 58.

As can be seen from FIG. 7, the processing device 58 has a first drive 86 for this purpose, which produces a first drive connection 88 with coupling means 90 of the mixing tool 84 in the receiving position. In addition, the processing device 58 has a second drive 92 which produces a second drive connection 94 to the comminution tool 82 in the receiving position. The first drive 86 and the second drive 92 can, as shown, be formed by parts of a common transmission, which in turn can be driven by a common motor 96. As an alternative to this, both drives 86, 92 can also be designed and activated separately (not shown).

Furthermore, the processing device 58 has a first actuator 98 by means of which a piston 100 of the collection container 8 can be displaced in the direction of the container opening 44 in order to empty the collection receptacle 34. In addition, the processing device 58 has a second actuator 102, by means of which a slide 104 of the processing container 52, on which the input/output connection 78 is held, can be displaced in order to empty the mixing receptacle 74 via this. Additionally or alternatively, the slide 104 may also be manually actuated, such as by the applicator 112 connected to the input/output connection 78. In this way, the mixing receptacle 74 can also be completely emptied independently of the processing device 58, for example in order to deliver a prepared application mass from the processing container 52 to the applicator 112.

Furthermore, the processing device 58 has electronics 106, by means of which the drives 86, 92 or their motor 96 and the actuators 98, 102 can be activated. Provision can be made here for the electronics 106 to run a preparation process in an at least partially automated, advantageously fully automated manner. The electronics 106 can be operated or programmed using a touch screen 108, for example. Image information generated by a camera 110, which is aimed at the mixing receptacle 74, can also be output, as shown in FIG. 6.

During a preparation process, in the receiving position according to FIG. 7, by activation of the motor 96, via the first drive 86, the whisk-shaped mixing tool 84 is set into motion and simultaneously, the disk-shaped comminuting tool 82 is rotated by the second drive 92. As a result, the tissue material G held in the collection receptacle 34 is comminuted and passes through the passage opening 80 into the processing container 52, where it can be mixed with the medium M.

By activating the first actuator 98, the piston 100 can be displaced in order to ensure complete comminution and complete delivery of the tissue material G to the mixing receptacle 74.

After the comminuted tissue material G has been delivered to the mixing receptacle 74, it is mixed with the medium M until a suitable application mass is produced. If required, additional medium M can be introduced into the mixing receptacle 74 for this purpose, in particular via the inlet/outlet connection 78A.

After the application mass is completed, the input/output connection 78 can be connected to the applicator 112 in the form of a syringe, which is drawn up with the application mass. In order to support the drawing of the applicator 112 and to be able to empty the mixing receptacle 74 as completely as possible, the second actuator 102 can be activated in order to displace the slide 104 with the input/output connection 78.

It should be noted that all elements and features of the various embodiments of the subject matter according to the invention described above can be swapped or combined with one another, provided that a swap or a combination thereof is not ruled out for technical reasons.

The invention claimed is:

1. A processing arrangement for tissue material removed from a patient and to be applied after processing, comprising:

a collection container which has a collection receptacle for receiving the tissue material removed by a tissue removal device;

a processing container which has a mixing receptacle for jointly receiving the tissue material and a liquid to pasty medium;

a connection device including a first fastener for attaching the collection container, a second fastener for attaching the processing container, one passage opening positioned between the collection receptacle and the mixing receptacle, and a comminuting tool rotatably mounted in the connection device and provided with at least one cutting element; and a processing device for mixing the tissue material and the medium, wherein the processing device is a separate component independent of the collection container and the processing container, and is configured to removably receive the connection device with the collection container and the processing container attached thereon.

2. The processing arrangement according to claim 1, wherein a comminuting tool is provided at the passage opening.

3. The processing arrangement according to claim 2, wherein the comminuting tool is formed by a disc which is rotatably mounted on the connection device and has at least one cutting element.

4. The processing arrangement according to claim 1, wherein a mixing tool projects into the mixing receptacle on the processing container.

5. The processing arrangement according to claim 4, wherein the mixing tool is formed by an agitator which is rotatably mounted on the processing container and can be driven by the processing device.

6. The processing arrangement according to claim 1, wherein the collection container has a closing element which can be adjusted between a closed position in which it closes the collection receptacle and an open position in which the collection receptacle is at least partially open.

7. The processing arrangement according to claim 6, wherein when the first fastener of the connection device is connected to a first counter-fastener of the collection container, the closing element can be brought automatically into a second open position in which a container opening of the collection container is open.

8. The processing arrangement according to claim 7, wherein the first fastener and the first counter-fastener form a first slide-in connection and the closing element is designed in the shape of a slide and can, by a sliding-in movement of the first fastener relative to the first counter-fastener, be displaced from the closed position into the second open position.

9. The processing arrangement according to claim 1, wherein the processing container has a closing element which can be adjusted between a final position in which it closes the mixing receptacle and a receiving position in which the mixing receptacle is open.

10. The processing arrangement according to claim 9, wherein the closing element can be brought into the receiving position automatically when the second fastener of the connection device is connected to a second counter-fastener of the processing container.

11. The processing arrangement according to claim 10, wherein the second fastener and the second counter-fastener form a second slide-in connection and the closing element is formed by a closure slide which can be transferred by a push-in movement of the second fastener relative to the second counter-fastener from the final position into the receiving position.

12. The processing arrangement according to claim 4, wherein the processing device has at least one drive and a processing receptacle for the connection device with the collection container and the processing container attached thereto, and the at least one drive forms a first drive connection with the mixing tool in a receiving position.

13. The processing arrangement according to claim 12, wherein the at least one drive in the receiving position also forms a second drive connection with a comminuting tool.

14. The processing arrangement according to claim 1, wherein the collection container has a piston for emptying the collection receptacle in the direction of the passage opening.

15. The processing arrangement according to claim 1, wherein the processing container has a closable input/output connection.

16. The processing arrangement according to claim 15, wherein a slide for emptying the mixing receptacle via the input/output connection is provided on the processing container.

17. The processing arrangement according to claim 16, wherein the processing device has at least one actuator for actuating the piston and/or the slide.

18. The processing arrangement according to claim 16, wherein the processing device has an electronic device for at least partially automated activation of at least one drive and/or at least one actuator.

19. The processing arrangement according to claim 1, wherein a camera is provided on the processing device for the visual recording of the mixing receptacle.

20. A collection/processing system comprising:

the processing arrangement according to claim 1, wherein the collection container can be detachably fixed to a connection housing of a collection device which is arranged for separating and collecting tissue material from a fluid flow between a tissue removal device and a vacuum device.

21. The collection/processing system according to claim 20, wherein the collection container has a flow portion of a connection path between a shaver-side flow connection which can be fluidically connected to the tissue removal device and a flow connection which can be fluidically connected to the vacuum device.

22. The collection/processing system according to claim 20, wherein the closing element of the collection container can be brought automatically from a first open position into the closed position when the collection container is removed from the connection housing.

23. A processing arrangement for tissue material removed from a patient and to be applied after processing, comprising:

a collection container having a collection receptacle for receiving the tissue material removed by a tissue removal device;

a processing container having a mixing receptacle for jointly receiving the tissue material and a liquid to pasty medium; and a processing device for mixing the tissue material and the medium, wherein the processing arrangement further comprises a connection device configured to jointly receive the collection container and the processing container to form a cassette-like slide-in unit, the connection device including:

first fasteners configured to attach the collection container;

second fasteners configured to attach the processing container; and a passage opening positionable between the collection receptacle and the mixing receptacle, wherein the cassette-like slide-in unit is configured to be slid into a processing receptacle of the processing device for carrying out a processing operation.

* * * * *